US009020606B2

(12) United States Patent
Yin

(10) Patent No.: US 9,020,606 B2
(45) Date of Patent: Apr. 28, 2015

(54) BRAIN ELECTRODE LEAD ANCHORING DEVICE

(75) Inventor: Weizhong Yin, Suzhou (CN)

(73) Assignee: Sceneray Co., Ltd., Suzhou (CN)

( * ) Notice: Subject to any disclaimer, the term of this patent is extended or adjusted under 35 U.S.C. 154(b) by 24 days.

(21) Appl. No.: 13/994,257

(22) PCT Filed: Dec. 12, 2011

(86) PCT No.: PCT/CN2011/083482
§ 371 (c)(1),
(2), (4) Date: Jul. 5, 2013

(87) PCT Pub. No.: WO2012/079478
PCT Pub. Date: Jun. 21, 2012

(65) Prior Publication Data
US 2014/0288625 A1 Sep. 25, 2014

(30) Foreign Application Priority Data
Dec. 15, 2010 (CN) .......................... 2010 1 0588332

(51) Int. Cl.
A61N 1/05 (2006.01)
(52) U.S. Cl.
CPC .................................... *A61N 1/0539* (2013.01)
(58) Field of Classification Search
CPC ................................................. A61N 1/0539
USPC .............. 604/175; 600/378; 607/115–116, 45
See application file for complete search history.

(56) References Cited

U.S. PATENT DOCUMENTS

| 4,328,813 | A | 5/1982 | Ray |
| 4,998,938 | A | 3/1991 | Ghajar et al. |
| 5,927,277 | A | 7/1999 | Baudino et al. |
| 5,954,687 | A | 9/1999 | Baudino |
| 6,044,304 | A | 3/2000 | Baudino |
| 6,210,417 | B1 | 4/2001 | Baudino et al. |
| 6,267,769 | B1 | 7/2001 | Truwit |
| 6,321,104 | B1 | 11/2001 | Gielen et al. |
| 6,394,779 | B1 | 5/2002 | Komazawa et al. |
| 7,004,948 | B1 * | 2/2006 | Pianca et al. .................. 606/129 |
| 7,454,251 | B2 | 11/2008 | Rezai et al. |

(Continued)

FOREIGN PATENT DOCUMENTS

CN 201899775 6/2011

OTHER PUBLICATIONS

International Search Report dated Mar. 8, 2012 in PCT Application No. PCT/CN2011/083482.

(Continued)

*Primary Examiner* — Paula J Stice
(74) *Attorney, Agent, or Firm* — Kilpatrick Townsend & Stockton LLP

(57) ABSTRACT

Disclosed is a device for anchoring a brain lead that includes an anchoring ring with a circular base and a flange joining together where the inner walls form an aperture define a passage of a lead. Outer walls engage with a burr hole to secure the ring to the cranium, and a septum is contained within the aperture of the anchoring ring. Because the septum is already placed in the aperture when the trocar is removed from the brain, the body of the brain lead is immediately clamped by the elastic material of the septum while the tip of trocar is removed from the slit of septum. Friction between the lead body and the elastic material prohibits any movement of the lead caused by handling.

19 Claims, 10 Drawing Sheets

(56) References Cited

U.S. PATENT DOCUMENTS

| | | | |
|---|---|---|---|
| 2003/0201239 A1* | 10/2003 | Hudak et al. | 215/247 |
| 2005/0182425 A1 | 8/2005 | Schulte et al. | |
| 2010/0023020 A1* | 1/2010 | Barker | 606/129 |
| 2010/0023100 A1 | 1/2010 | Barker | |

OTHER PUBLICATIONS 11848066.4-1652 / 2653188 , Extended European Search Report dated May 282, 2014.

* cited by examiner

BRAIN ELECTRODE LEAD ANCHORING DEVICE

RELATED APPLICATIONS

This application is a 35 U.S.C. §371 national phase application of PCT Application PCT/CN2011/083482, filed May 12, 2011, which claims priority to CN 201010588332.8, filed Dec. 15, 2010. The entire content of each of these applications is incorporated herein by reference.

TECHNICAL FIELD

The present invention generally relates to the field of implanted medical system, and more particularly relates to a device for anchoring brain lead or other catheter or the like onto cranium in an implantable medical device system.

BACKGROUND

An implantable medical device system typically comprises an implantable nerve stimulation system, an implantable cardiac stimulation system (known as cardiac pacemaker), and an implantable medication infusion system, where the implantable nerve stimulation system comprises a deep brain stimulation (DBS), an implantable cortical nerve stimulation (CNS), an implantable spinal cord stimulation (SCS), an implantable sacral nerve stimulation (SNS), and an implantable vagus nerve stimulation (VNS), etc.

For an example, the implantable deep brain stimulation system mainly comprises a pulse generator and lead implanted inside the body, and a control device outside the body, where the pulse generator is connected with the lead such that the pulse generated by the pulse generator is transmitted to the lead. The pulse generated by the pulse generator is delivered to particular nerve sites and restore the normal functionalities of the brain by means of electrical stimulation.

A clinician firstly determines the target in the patient's brain by means of a stereotactic surgery during the process of implantation operation. Then, the clinician drills a small hole in the patient's cranium and inserts a brain lead through the hole to the desired brain target site. The clinician uses a test stimulator to test the efficiency of the stimulation. If the effect of stimulating therapy is desirable, the brain lead is then anchored to the cranium using an anchoring device.

A device for anchoring a brain lead, described in the U.S. Pat. No. 4,328,813, typically comprises a socket and a plug. The plug is placed into the socket after the brain lead is inserted in the brain. The brain lead is secured by friction force between the socket and the plug.

However, the disadvantage of this method is obvious: the engagement between the plug and socket during the insertion inevitably brings the lead along with the plug's downward movement, thus causes the dislodgement of the electrodes from the desired stimulation site. Such dislodgement may result in unexpected clinical consequences. Moreover, the top portion of the plug sits over the flange portion of socket, which adds additional thickness to the device. Such thick foreign material on the cranium will cause discomfort or other complication to the patient.

SUMMARY OF THE INVENTION

In contrast with the disadvantages in the prior art, the present invention provides a reliable device to fix the brain lead to the skull and to ensure the electrodes of the brain lead at the desired target site. The lead dislodgement is eliminated during operation. The anchoring device is easy to use.

The present invention includes: an anchoring ring comprising a circular base and a flange joining together where the inner walls form an aperture defining a passage of a lead and the outer walls engage with a burr hole to secure the said ring to the cranium; a septum contained within the aperture of the anchoring ring, comprising a slit in its center to allow the brain lead to pass through.

Preferably, the slit cuts through material of the septum completely or partially.

Preferably, the slit is a straight cut, curve cut, or cross cut.

Preferably, the slit separates the septum partially or completely into two halves or the slit cuts in the middle without separating the septum.

Preferably, the septum comprises at least one protrusion mates with a groove or protrusion or thread provided on inner walls of the aperture to secure the septum.

Preferably, a bottom surface of the septum is concaved.

Preferably, the septum is made of an elastic material.

Preferably, the inner wall of the aperture comprises a set of protrusions at the bottom thereof so as to prevent said septum from dropping out of the aperture while lead insertion.

Preferably, the anchor ring comprises a flange portion which has at least one lead groove to accommodate the brain lead, and the said base has a notch.

Preferably, the septum comprises at least one blind hole on the top surface to provide guide while the septum is inserted into the said aperture.

The invention has the following advantages comparing with the prior art: due to the fact the septum is already placed in the aperture when the trocar is removed from the brain, the body of the brain lead is immediately clamped by the elastic material of the septum while the tip of trocar is removed from the slit of septum. The friction between the lead body and the elastic material prohibits any movement of the lead caused by handling of lead during or after the operation. Thus the desired placement of electrodes inside the brain is ensured in the entire procedures.

Moreover, the septum is contained within the aperture and the top of the septum is below the flange portion of the ring, therefore the device is less protruding comparing with the prior art, thereby causes less discomfort to the patient.

Figure 1:
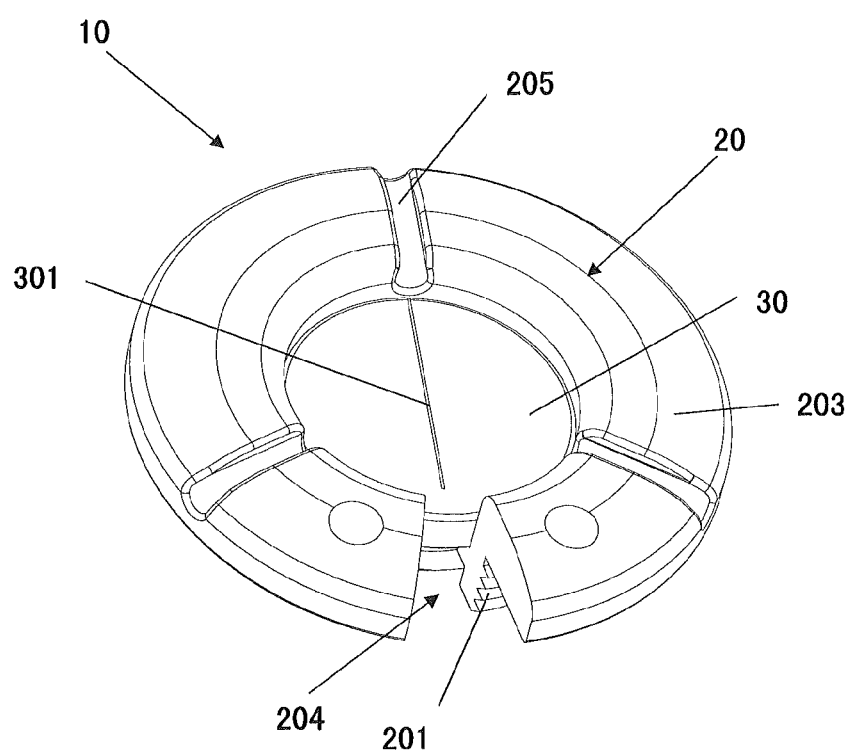
FIG. 1 is a schematic structure view of the invention (the first embodiment)
Figure 2:
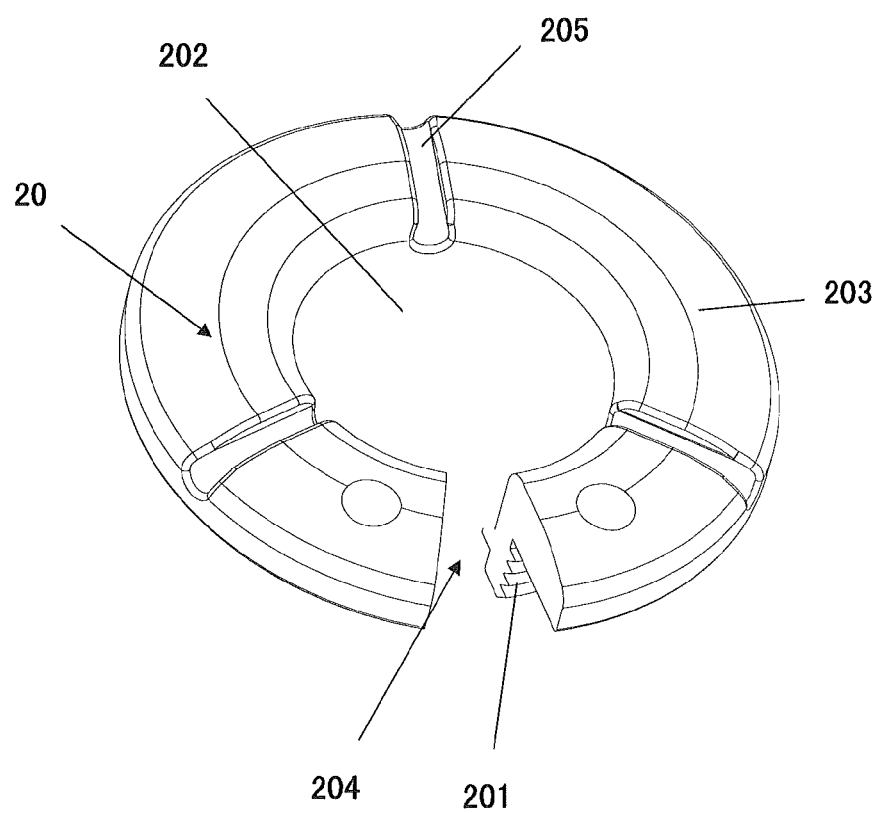
FIG. 2 is a three-dimensional schematic structure view of the cranial ring of the invention (the first embodiment)
Figure 3:
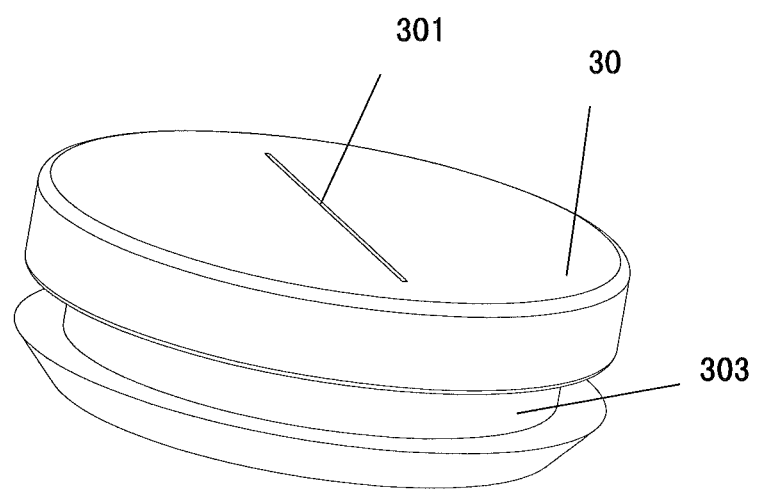
FIG. 3 is a schematic structure view of the cranial septum of the invention (the first embodiment)
Figure 4:
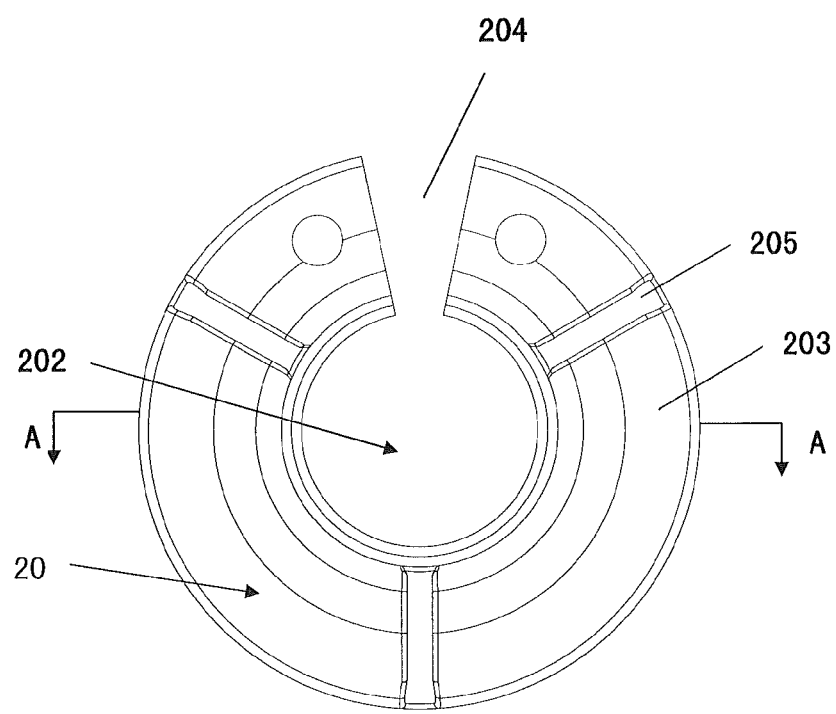
FIG. 4 is a schematic structure top view of the cranial ring of the invention (the first embodiment)
Figure 5:
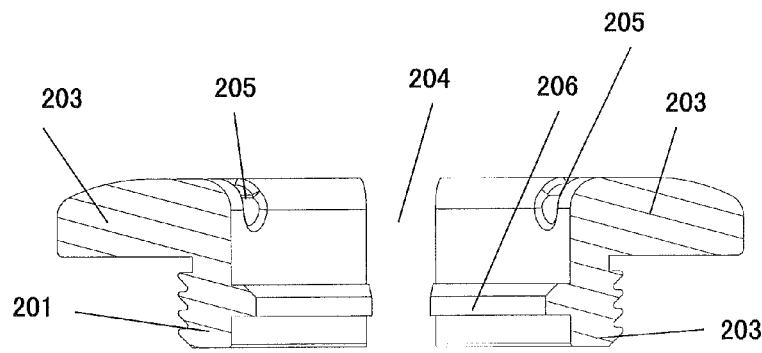
FIG. 5 is a schematic sectional view taken in the direction of A-A in FIG. 4 (the first embodiment)

Where:

10: device for anchoring brain lead; 20: cranial ring; 201: circular base; 202: lead aperture; 203: flange portion; 204: notch; 205: lead groove; 206: protrusion; 30: cranial septum; 301: slit; 302: pick-and-place portion; 303: recessed portion.

DETAILED DESCRIPTION

The invention will be further described hereinafter with reference to the accompanying drawings.

The First Embodiment

As shown in FIGS. 1-5, a device for anchoring brain leads 10 comprises a cranial ring 20 and a cranial septum 30. The anchoring ring 20 comprises a circular base 201 and a flange portion 203 joining together where the inner walls form an aperture 202 defining a passage of a lead and outer walls engage with a burr hole to secure said ring 20 to the cranium. The septum 30 is contained within the aperture 202 of the anchoring ring 20, comprising a slit 301 in its center to allow the brain lead to pass through.

Figure 6:
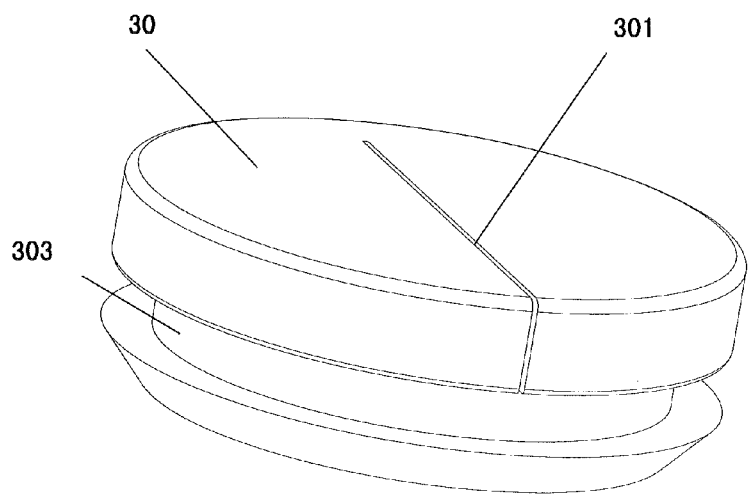
FIG. 6 is a schematic structure view showing cutting a shallow slit in the cranial septum of the invention.
Figure 7:
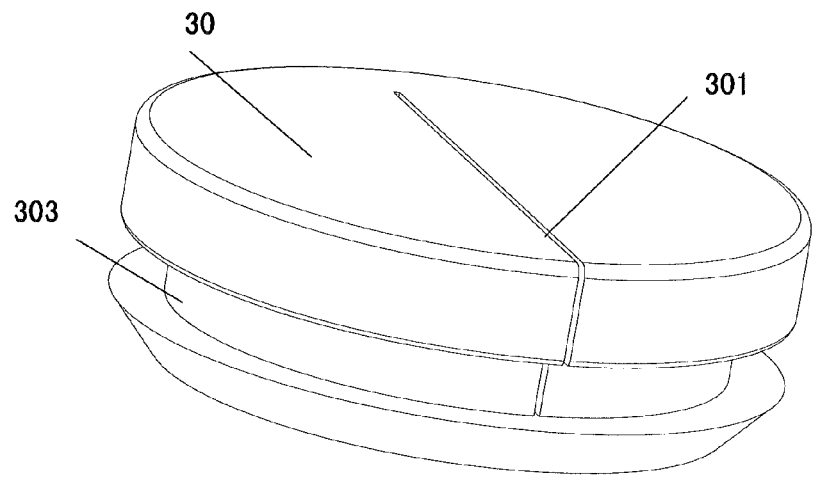
FIG. 7 is a schematic structure view showing cutting a deep slit in the cranial septum of the invention.
Figure 8:
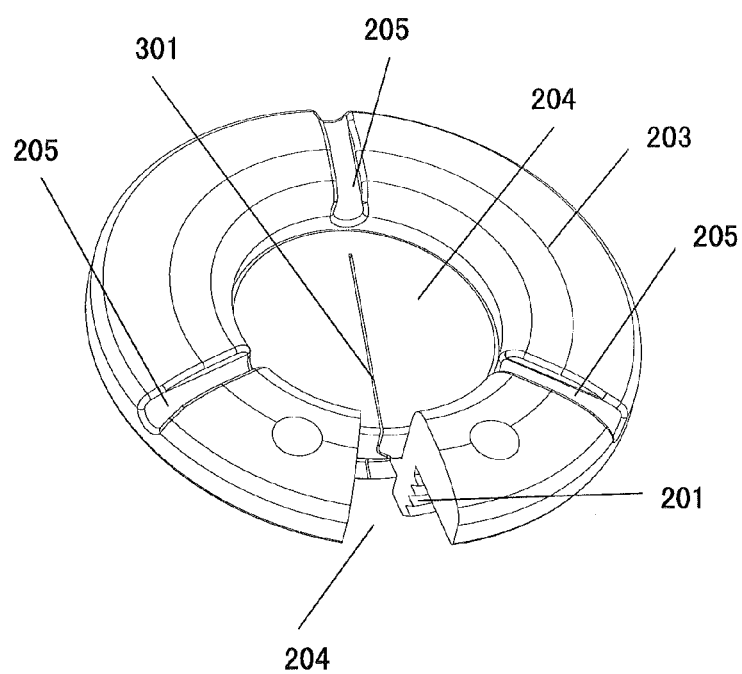
FIG. 8 is a schematic structure view of the invention (the second embodiment)
Figure 9:
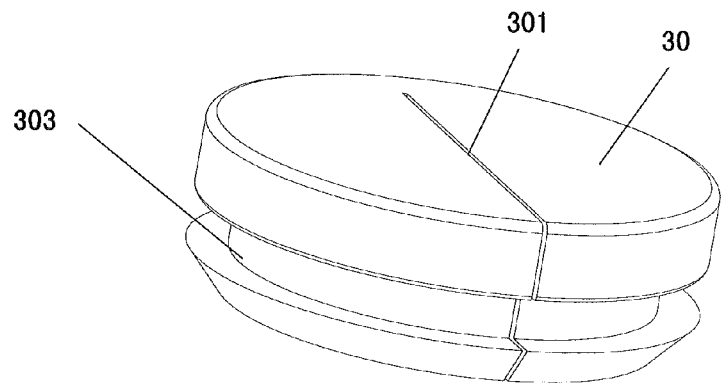
FIG. 9 is a schematic structure view of the cranial septum of the invention (the second embodiment)
Figure 10:
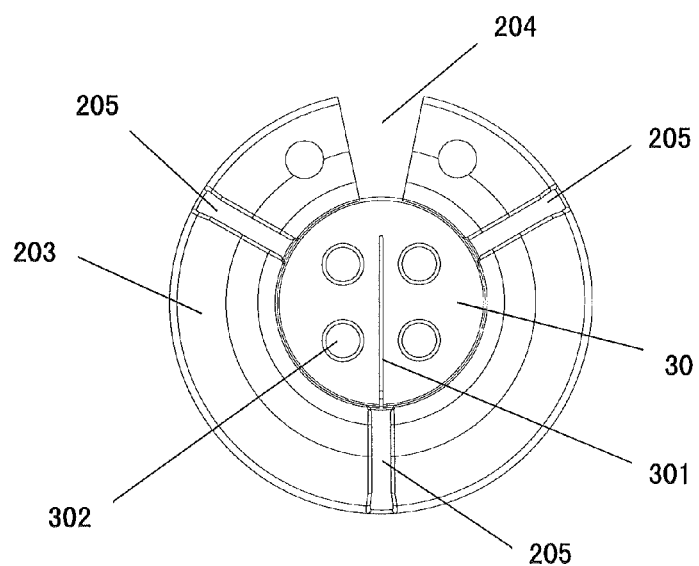
FIG. 10 is a schematic structure top view of the cranial ring of the invention (the second embodiment)
Figure 11:
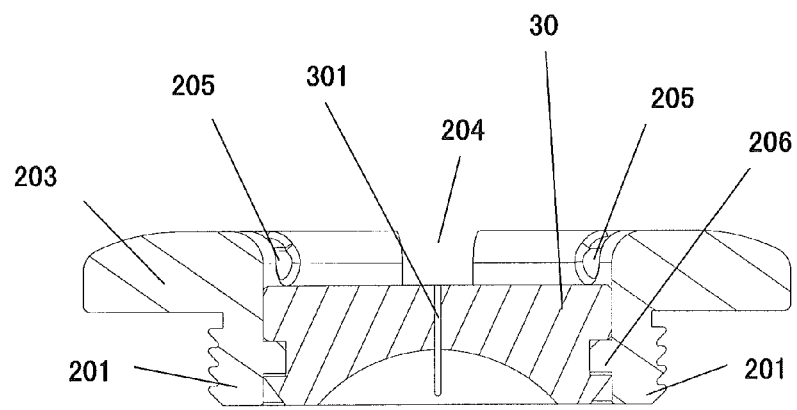
FIG. 11 is a schematic sectional view taken in the direction of B-B in FIG. 4 (the second embodiment)

In this embodiment, the slit 301 is a through-slit through which the clinician passes a trocar into the brain of patient for use. Alternatively, the slit can be shallow slit or deep slit. As shown in FIGS. 6 and 7, when in use, the clinician just need to use the trocar to pierce the shallow slit or deep slit so as to insert the brain lead to a pre-calculated depth through the inner hole of the trocar.

The through-slit and the deep/shallow slit can be a straight, a curve or a cross cut. In this embodiment, the slit is a "-" shaped straight cut. The outer wall of the cranial septum 30 is provided with a recessed portion 303 to closely and firmly mate with the inner wall of the lead aperture 202. With the mate of the recessed portion 303 and the aperture 202, the cranial septum 30 can not move when reaching the preset site, thereby preventing the septum from dropping out of the aperture 202. In other embodiment, the outer wall of the cranial septum 30 can be provided with protrusions or thread to mate with the inner wall of the lead aperture.

The circular base 201 of the cranial ring 20 extends outwardly to form a flange portion 203. Since a notch 204 is provided to the circular base 201, the flange portion 203 is flexible for mating with the holes in various diameters drilled by the clinicians. At least one lead groove is provided on flange portion 203 to receive the lead. According to the present embodiment, three grooves are provided on flange portion 203. The lead is anchored to the cranial septum 30 when inserted into the preset target site by the clinician. A part of the lead outside of the brain of the patient is received by the closest one of the lead grooves, which is easy to operate.

When in use, the cranium septum 30 is inserted into the cranial ring 20. The well mated cranium septum 30 and cranial ring 20 is inserted into the cranial burr hole of the patient. Then, the lead is inserted to the pre-calculated depth through the inner hole of a trocar following that the trocar is inserted in place through the slit 301, which is the "-" type and located at the center of the septum 30 according to the present embodiment. If it is found that the pre-calculated stimulation spot does not face the center of the septum 30 or not face the slit 301, the septum 30 and the ring 20 have to be adjusted with respect to each other at the same plane, and the lead groove 205 can face the trocar, for example, rotating the septum 30 along the recessed portion or protrusion 206 at the plane by using a dedicated auxiliary tool.

The trocar is taken out of the brain in the direction of the axis of the trocar after the adjusting and testing, and the lead is anchored and is kept in the state of being anchored due to the septum 30 with flexibility. Thus, the deviation in the axis or the plane is avoided. Finally, the lead is anchored to the lead groove 205 which is the closest one to the end face of the ring 20 after the wire of the lead is taken out. The invention has the following advantages comparing with the prior art: due to the fact the septum 30 is already placed in the aperture 202 when the trocar is removed from the brain, the body of the brain lead is clamped by the elastic material of the septum 30 immediately during the removal of the trocar. The friction between the lead body and the elastic material prohibits any movement of the lead caused by handling of lead during the operation. Thus the desired placement of electrodes inside the brain is ensured in the entire procedures.

The bottom surface of the cranial septum 30 is concaved so that the cranial septum 30 is soft in entirety and flexible, which enables the trocar easily inserted and the lead anchored without any damage to the lead after the trocar is removed.

The cranial septum 30 is made of an elastic material, such as silica gel. This also enables the trocar to be easily inserted and the lead can be anchored without any damage after the trocar is removed. Another set of protrusions provided at the bottom of the inner wall of the aperture 202 of the ring 20 to prevent the septum 30 dropping out of the aperture 202 while lead insertion. The protrusion 206 on the ring 20 mates with the recessed portion 303 of the septum 30. One or more pick-and-place portions 302 is provided at the top face of the cranial septum 30 to facilitate the picking and placing of the device for anchoring a brain lead 10 during the operation. There are four pick-and-place portions 302 according to the present embodiment. A dedicated auxiliary anchoring tool or medical tweezers can be used to pick or place the septum 30.

The Second Embodiment

As shown in FIGS. 8 to 11, the second embodiment differs from the first one in the slit 301. According to the second embodiment, one end of the slit 301 extends to the edge of the outside wall of the cranial septum 30 to form an edge-engaging through slit. However, the use of the device for anchoring a brain lead is different from that according to the first embodiment.

When in use, the cranial ring 20 is inserted to the cranial burr hole of the patient. The trocar is then inserted in place after cranial ring 20 mates well with the burr hole. Then, the trocar is anchored by a dedicated clamp while the nerve stimulation lead is inserted to a pre-calculated depth through the inner hole of the trocar. After the clinicians completes the adjustment and test, as shown in FIG. 7, the slit 301 of the cranium septum 30 is expanded sideways by hand to form a notch. The trocar which is aligned in position and contains the lead is clamped within the cranium septum 30 and further aligned with the protrusion 206 of the cranial ring 20; then, the cranium septum 30 is pressed downwardly by hand or dedicated tool such that the cranium septum 30 and the cranial ring 20 are completely mated in place so as to anchor the brain lead. The next operational steps and manners are the same as those described above.

The Third Embodiment

Figure 12:
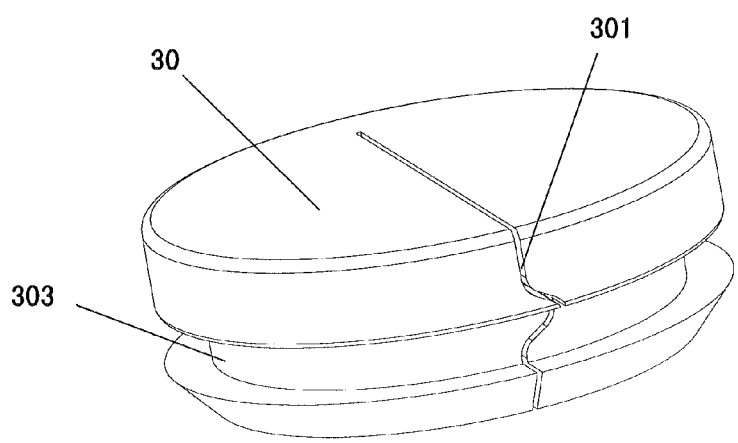
FIG. 12 is a schematic structure view of the cranial septum of the invention (the third embodiment)

As shown in FIG. 12, the slit 301 of the cranium septum 30 in this embodiment is an edge-engaging curve slit rather than the "-" shaped edge-engaging straight slit. The operational steps for the clinicians are substantially the same as those in the second embodiment. When the cranium septum 30 is inserted into the lead aperture 202 of the cranial ring 20, the cranium septum 30 and the cranial ring 20 are well mated by the mating between the recessed portion 303 of the cranium septum 30 and the protrusion 206 of the ring 20. Meanwhile, the edge-engaging curve slit makes it easy to determine whether the cranium septum 30 is inserted in position.

The Fourth Embodiment

Figure 13:
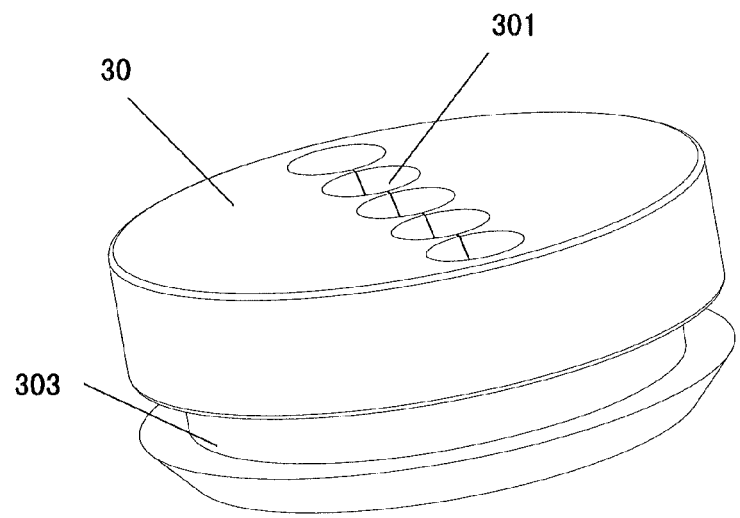
FIG. 13 is a schematic structure view of the cranial septum of the invention (the fourth embodiment)

As shown in FIG. 13, the slit 301 of the cranium septum 30 in this embodiment is composed of a plurality of circular slits that are arranged along the diameter. The circular slits can be through-holes or deep cuts or shallow cuts. The operational steps for the clinicians are substantially the same as those in the first embodiment. In case of deep slits or shallow slits, the clinicians have to firstly pierce the circular slits when inserting the trocar; and in case of through-holes, it would be convenient and labor saving for the clinicians to insert the trocar.

The Fifth Embodiment

Figure 14:
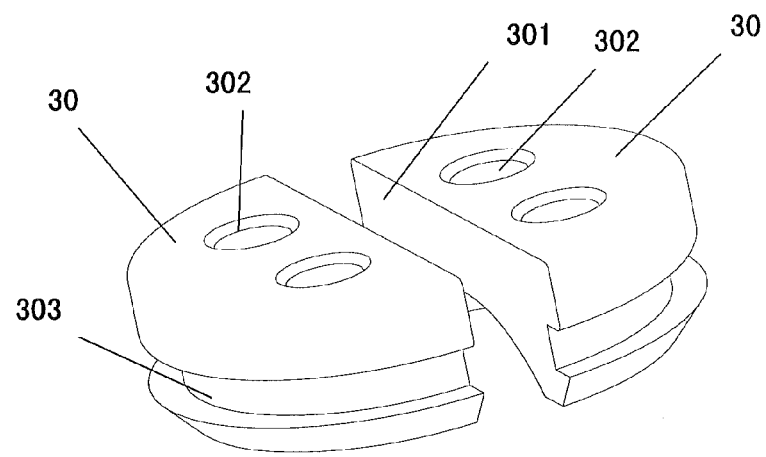
FIG. 14 is a first schematic structure view of the cranial septum of the invention (the fifth embodiment)
Figure 15:
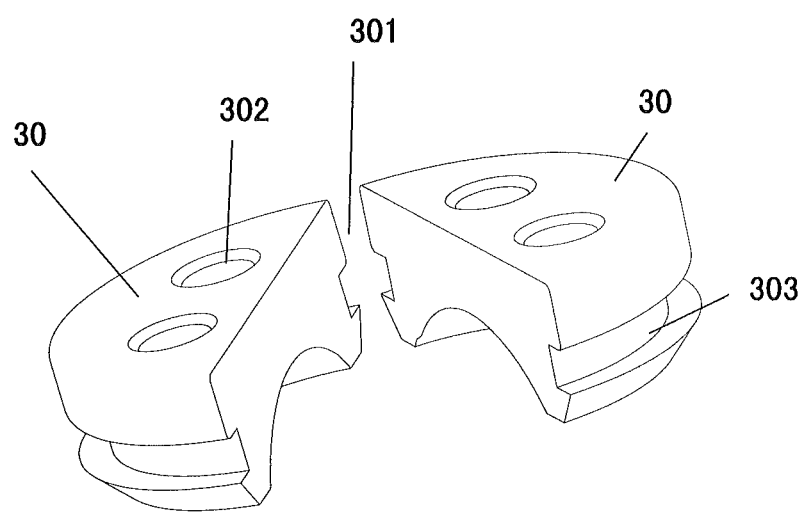
FIG. 15 is a second schematic structure view of the cranial septum of the invention (the fifth embodiment)

As shown in FIGS. 14 and 15, the fifth embodiment differs from the second embodiment in that both ends of the through-hole 301 of the cranium septum 30 extend to the edge of the outside wall of the cranium septum 30. That is, the cranium septum 30 forms two semi-circles that are separated from each other. The through-hole formed between the two semi-circles is used for passing and anchoring the brain lead.

During operation, the cranial ring 20 is firstly inserted into the cranial burr hole of the patient. The trocar is then inserted to the preset position after the cranial ring 20 mates well with the burr hole. Then, the trocar is anchored by a dedicated clamp while the nerve stimulation lead is inserted to a pre-calculated depth through the inner hole of the trocar. After the clinicians complete the adjustment and test, both of the semi-circles of the septum 30 inserted into the aperture 202 of the ring 20 to clamp the trocar there between, and then align with the protrusion 206 or snapping slot of the ring 20. The two semi-circles are further pressed downwardly by hand or dedicated tool so that the cranium septum 30 and the cranial ring 20 are well mated in place. The next operational steps and manners are the same as those described above. The invention can also be susceptible to many other embodiments without departing from the spirit and essence of the invention. Various corresponding modifications and variations can be made to the invention by those skilled in the art according to the invention, which all fall within the scope of protection of the appended claims.

What is claimed is:

1. A device for anchoring a brain lead within a cranial burr hole of a cranium while closing the cranial burr hole, comprising:
an anchoring ring with inner walls, the anchoring ring comprising a circular base and a flange joining together where the inner walls form an aperture defining a passage for the brain lead, the anchoring ring further comprising outer walls configured to engage with the cranial burr hole to secure said anchoring ring to the cranium;
a septum contained within the aperture of the anchoring ring and comprising a slit in its center to allow the brain lead to pass through such that the slit extends along a curve in a vertical direction through an entire thickness of the septum such that the vertically curved slit is configured to retain the brain lead in position using friction.

2. The device of claim 1, wherein the slit comprises an elongated rectangular cross-section and is configured to reach an outer edge of the septum.

3. The device of claim 1, wherein the slit comprises at least one circular hole.

4. The device of claim 1, wherein the slit is configured to completely sever the septum into at least two pieces.

5. The device of claim 4, wherein the at least two pieces comprise two halves that are each approximately semi-circular.

6. The device of claim 1, wherein the septum comprises at least one protrusion configured to mate with a feature provided on the inner walls of the aperture to secure the septum.

7. The device of claim 6, wherein the inner walls comprise a set of protrusions disposed at the bottom of the inner walls so as to prevent said septum from dropping out of the aperture during lead insertion.

8. The device of claim 6, wherein the feature provided on the inner walls of the aperture is a recessed portion.

9. The device of claim 8, wherein the recessed portion is a slot with a shape that approximately matches the at least one protrusion.

10. The device of claim 1, wherein a bottom surface of the septum is concave.

11. The device of claim 1, wherein the septum is made of an elastic material.

12. The device of claim 1, wherein the flange has at least one lead groove to accommodate the brain lead, and the circular base has a notch.

13. The device of claim 12, wherein the at least one lead groove is disposed on an upper surface of the flange extending in a radial direction.

14. The device of claim 1, wherein the septum comprises at least one blind hole on a top surface of the septum.

15. The device of claim 1, wherein the slit extends vertically through a portion of the septum along a straight line.

16. The device of claim 1, wherein the vertically curved slit extends along a curved line with a general 'S' shape through the septum.

17. A device for anchoring a brain lead within a cranial burr hole of a cranium while closing the cranial burr hole, the device comprising:
an anchoring ring comprising:
a circular base and a flange joined together where inner walls of the anchoring ring form an aperture defining a passage for the brain lead;
outer walls configured to engage with the cranial burr hole to secure the anchoring ring to the cranium, and
a septum contained within the aperture of the anchoring ring, wherein a center of the septum comprises a slit configured to allow passage of the brain lead through the septum,
wherein the slit extends along a curve in a vertical direction through a thickness of the septum such that the vertically curved slit is configured to retain the brain lead in position using friction.

18. The device of claim 17, further comprising a notch that separates a first end of the anchoring ring from a second end of the anchoring ring such that the anchoring ring is discontinuous in a circumferential direction of the anchoring ring, wherein the notch separates the first end of the anchoring ring from the second end of the anchoring ring throughout an entire thickness of the anchoring ring.

19. The device of claim 18, wherein the notch extends from a top surface of the anchoring ring to a bottom surface.

\* \* \* \* \*